(12) United States Patent
Wigbers et al.

(10) Patent No.: US 8,445,726 B2
(45) Date of Patent: May 21, 2013

(54) PROCESS FOR PREPARING UNSYMMETRIC SECONDARY TERT-BUTYLAMINES IN THE LIQUID PHASE

(75) Inventors: Christof Wilhelm Wigbers, Mannheim (DE); Christoph Mueller, Mannheim (DE); Johann-Peter Melder, Boehl-Iggelheim (DE); Bernd Stein, Alsbach-Haehnlein (DE); Harald Meissner, Hassloch (DE); Gerd Haderlein, Gruenstadt (DE); Norbert Gutfrucht, Lambrecht (DE)

(73) Assignee: BASF SE, Ludwigshafen (DE)

( * ) Notice: Subject to any disclaimer, the term of this patent is extended or adjusted under 35 U.S.C. 154(b) by 114 days.

(21) Appl. No.: 13/080,080

(22) Filed: Apr. 5, 2011

(65) Prior Publication Data

US 2011/0251433 A1    Oct. 13, 2011

Related U.S. Application Data

(60) Provisional application No. 61/321,517, filed on Apr. 7, 2010.

(51) Int. Cl.
*C07C 209/26* (2006.01)

(52) U.S. Cl.
USPC ............ 564/473; 564/397; 564/398; 564/446

(58) Field of Classification Search
None
See application file for complete search history.

(56) References Cited

U.S. PATENT DOCUMENTS

| | | | |
|---|---|---|---|
| 2011/0137029 A1 | 6/2011 | Kubanek et al. | |
| 2011/0137030 A1 | 6/2011 | Kubanek et al. | |

FOREIGN PATENT DOCUMENTS

| | | |
|---|---|---|
| DE | 101 22 758 A1 | 11/2002 |
| EP | 1 312 600 B1 | 8/2004 |
| EP | 1 312 599 B1 | 3/2006 |
| GB | 1116610 | 6/1968 |
| WO | WO 2004/009529 A1 | 1/2004 |
| WO | WO 2009/084538 A1 | 7/2009 |

OTHER PUBLICATIONS

U.S. Appl. No. 13/119,948, filed Mar. 18, 2011, Ernst, et al.
U.S. Appl. No. 13/080,885, filed Apr. 6, 2011, Mueller, et al.
International Search Report issued May 24, 2011, in Patent Application No. PCT/EP2011/055372 (with English Translation of Category of Cited Documents).
Leonard M. Weinstock, et al., "Synthesis of the β-Adrenergic Blocking Agent Timolol from Optically Active Precursors", Journal of Organic Chemistry, vol. 41, No. 19, XP 2634073, 1976, pp. 3121-3124.
Zhenliang Chen, et al., "The synthesis of baclofen and GABOB via Rh(II) catalyzed intramolecular C-H insertion of α-diazoacetamides", Tetrahedron, vol. 61, No. 6, XP 25382974, 2005, pp. 1579-1586.
"Houben-Weyl, Methoden der organischen Chemie", Georg Thieme Verlag, 4th Edition, vol. XI/1, XP 2634072, 1959, pp. 618-634.
Jeffrey C. Bottaro, et al., "Improved Synthesis of Cubane-1,2,4,7-tetracarboxylic Acid", Journal of Organic Chemistry, vol. 56, 1991, pp. 1305-1307.
Martin Newcomb, et al., "Mechanism of Reduction of Trityl Halides by Lithium Dialkylamide Bases", Journal of the American Chemical Society, vol. 112, 1990, pp. 5186-5193.
Yu. D. Smirnov, et al., "Electrochemical Reductive Amination: II. Amination of Aliphatic Aldehydes With Primary Amines", Russ. J. Org. Chem. (Zhurnal Organicheskoi Khimii), vol. 28, No. 3, 1992, pp. 374-380.
Silvia Gomez, et al., "The Reductive Amination of Aldehydes and Ketones and the Hydrogenation of Nitriles: Mechanistic Aspects and Selectivity Control", Advanced Synthesis & Catalysis, vol. 344, No. 10, 2002, pp. 1037-1057.
John J. Birtill, et al. "Optimization of Reaction Conditions in Single-Stage Reductive Amination of Aldehydes and Ketones", Catalysis of Organic Reactions, vol. 75, 1998, pp. 255-271.
U.S. Appl. No. 13/516,479, filed Jun. 15, 2012, Maegerlein, et al.
U.S. Appl. No. 13/516,521, filed Jun. 15, 2012, Maegerlein, et al.

*Primary Examiner* — Brian J Davis
(74) *Attorney, Agent, or Firm* — Oblon, Spivak, McClelland, Maier & Neustadt, L.L.P.

(57) ABSTRACT

The present application relates to a process for preparing unsymmetric secondary tert-butylamines which, as well as the tert-butyl radical, also comprise an alkyl, cycloalkyl or benzyl radical. They are prepared by reacting corresponding aldehydes with tert-butylamine and hydrogen in the presence of hydrogenation catalysts (reductive amination) in the liquid phase.

20 Claims, No Drawings

PROCESS FOR PREPARING UNSYMMETRIC SECONDARY TERT-BUTYLAMINES IN THE LIQUID PHASE

This application claims priority to U.S. provisional application Ser. No. 61/321,517, filed Apr. 7, 2010.

The present application relates to a process for preparing unsymmetric secondary tert-butylamines which, as well as the tert-butyl radical, also comprise an alkyl, cycloalkyl or benzyl radical. They are prepared by reacting corresponding aldehydes with tert-butylamine and hydrogen in the presence of hydrogenation catalysts (reductive amination) in the liquid phase.

Secondary amines are important, industrially utilized substances. They serve, for example, as polymerization and curing catalysts for the production of polymer moldings based on epoxides and polyurethanes, as corrosion inhibitors and as starting materials for flocculants and detergents. In addition, secondary amines are used as intermediates in crop protection.

WO 2009/084538 describes unsymmetric amines with tert-butyl and alkyl radicals for preparation of vulcanization accelerants for rubber.

Secondary amines are obtainable by alkylating primary amines with alkyl halides, by acetylation of primary amines and subsequent reduction of the carbonyl group with lithium aluminum hydride, and by reductive, especially hydrogenating, amination of aldehydes with primary amines.

This is in principle also true of unsymmetric secondary amines comprising tert-butyl groups:

J. C. Bottaro et al. state, in Journal of Organic Chemistry, 1991, 56, pages 1305 to 1307, that ethyl-tert-butylamine is preparable by reaction of tert-butylamine with ethyl bromide in a molar ratio of 3:1 with 85% yield. Disadvantages of this process are that the hydrogen bromide obtained leads to occurrence of salts after neutralization, that excess tert-butylamine has to be removed and recycled for economic reasons, and that corrosion problems occur.

M. Newcomb et al. describe, in contrast, in Journal of the American Chemical Society, 1990, 112, pages 5186 to 5193, acetylating tert-butylamine with acetic anhydride (40% yield) and reducing the resulting N-tert-butylacetamide with lithium aluminum hydride to ethyl-tert-butylamine. However, the process has two stages, enables only low yields and is afflicted the occurrence of oxygen-containing aluminum compounds.

Yu. Smirnow et al. state, in Zhurnal Organicheskoi Khimii (1992), 28 (3), pages 461 to 467, that ethyl-tert-butylamine is also preparable by electrochemical reductive amination of acetaldehyde with tert-butylamine over lead cathodes in 60% yield. A particular disadvantage is the low yields.

The hydrogenating amination of aldehydes with primary amines in the presence of hydrogenation catalysts to give corresponding unsymmetric secondary amines is likewise known. In this context, it is necessary, as already described in GB-A 1,116,610, page 2 column 1 lines 1 to 4, to suppress the further reaction thereof with the particular aldehydes to undesired tertiary amines as far as possible, in order to be able to achieve high yields of secondary amines. Moreover, it is necessary to find reaction conditions and hydrogenation catalysts with which the side reactions—aldehyde decarbonylation, aldehyde hydrogenation to alcohols and aldol condensation between two aldehyde molecules—are very substantially prevented.

Advanced Synthesis & Catalysis, 2002, 344, page 1041, chapter 3.1, first paragraph, states that, in the reaction of an amine with a carbonyl compound, yields and selectivities depend to a high degree on the steric hindrance of the starting compounds. This steric hindrance also plays a role in the region of the amine function, as explained in chapter 3.1, third paragraph, and scheme 10. For instance, the reductive amination of acetone with 2,4,6-trimethylaniline forms the secondary amine only in 36% yield, but with 98% yield with aniline. A reduced reaction rate of the reductive amination can also lead to the carbonyl compound being hydrogenated to the corresponding alcohol to a higher degree. The processes described in the prior art never describe the use of sterically hindered tert-butylamine, since smaller yields of the inventive secondary tert-butylamine I and greater amounts of alcohol as a result of the hydrogenation of the particular aldehyde have to be expected here.

DE-A 101 22 758 describes a process for preparing unsymmetric secondary amines, in which aldehyde and primary amine are fed into the reactor in the liquid phase separately from one another but simultaneously, and reacted there with hydrogen over a nickel-comprising catalyst. The process is particularly suitable for preparing N-ethyl-n-propylamine, as evident in example 4 by the gas chromatography yield of 92%, based on propionaldehyde. A disadvantage is, as already shown by example 1 in DE-A-101 22 758, continuous preparation of N-ethyl-n-propylamine requires high pressure around 8 MPa and a five-fold molar excess of ethylamine, based on propionaldehyde. Accordingly, a large amount of ethylamine has to be removed by distillation and recycled into the hydrogenation. Furthermore, this disclosure does not describe the preparation of secondary tert-butylamines.

Houben/Weyl, Methoden der organischen Chemie [Methods of Organic Chemistry], fourth edition, volume XI/1, Stickstoffverbindungen II [Nitrogen Compounds II], Georg-Thieme-Verlag, 1959, page 620, describes the preparation of n-butyl-i-butylamine. For this purpose, a stirred autoclave is initially charged with i-butylamine, Raney nickel and methanol as a solvent. At 100° C. and a hydrogen pressure of 100 bar, approximately equimolar amounts of n-butyraldehyde, based on initially charged amine, are supplied continuously within 65 minutes. After distillative workup, an n-butylisobutylamine yield of 86% was achieved. Disadvantages of this process are the high pressure and the use of a solvent which has to be removed and recycled.

On the other hand, Chem. Ind. Dekker describes, in Catalysis of Organic Reactions, 75, pages 266 to 270, 1998, the preparation of N-ethyl-n-butylamine. Here too, the autoclave is initially charged with the amine, in this case ethylamine, together with the catalyst, in order subsequently to add n-butyraldehyde at 80° C. and 24 bar over a period of 4.5 to 5 hours. In contrast to the disclosure in Houben/Weyl, the molar ratio of amine to aldehyde here is, however, 2.6 to 1. In spite of this, in the presence of nickel catalysts, reaction outputs which comprise only about 64% N-ethyl-n-butylamine are obtained. With noble metal catalysts (5% Pd, 5% Pt, 5% Rh, 5% Ru on activated carbon), the N-ethyl-n-butylamine contents of the reaction outputs are, however, 82 to 96%. Disadvantages of this process are the low product of value yields in the presence of nickel catalysts and the necessity of removing and recycling excess amine. Here too, the preparation of secondary tert-butylamines I is not described.

In GB-A 1,116,610 too, amine is initially charged in a reactor together with a hydrogenation catalyst and admixed with an aldehyde in the presence of hydrogen. N-methylbutylamine can thus be prepared according to example 3 at 100° C. and 30 bar in 97% yield from n-butyraldehyde and methylamine in the presence of Raney nickel. The molar ratio of methylamine to n-butyraldehyde is 1.25 to 1. A disadvantage of this process is that large amounts of about 3% aqueous sodium hydroxide solution have to be added to prevent the formation of tertiary amines and removed again after the reaction. The preparation of secondary tert-butylamines I is not described explicitly here either.

The reaction conditions and the results of the reductive aminations in the four preceding documents are compiled in table 1 below.

TABLE 1

| Reference | Prim. amine | Aldehyde | Molar ratio of aldehyde to amine | Catalyst | Addition | Addition time | Pressure [bar] | Solvent or addition | Yield [%] |
|---|---|---|---|---|---|---|---|---|---|
| DE 10122758 | Ethyleneamine | Propionaldehyde | 1:5 | Ni | Simultaneous addition of both reactants | — | 80 | — | 92 |
| Catalysis of Org. Reactions | Aq. methylamine (70% strength) | n-Butyraldehyde | 1:2.6 | Ni | Amine initially charged | 5 | 24 | — | 64 |
| | | | | 5% Pd/C | | | | — | 83 |
| Houben-Weyl | i-Butylamine | n-Butyraldehyde | 1:1 | Ra—Ni | | 1 | 100 | CH$_3$OH | 86 |
| GB 1116610 ex. 2 | Methylamine | n-Butyraldehyde | 1:1.25 | Ra—Ni | | 5 | 100 | approx. 3% NaOH | 97 |

It was therefore an object of the present invention to provide a process for reductive amination of aldehydes with tert-butylamine in the presence of hydrogenation catalysts, which avoids the abovementioned disadvantages. The process should afford high yields of unsymmetric secondary amines without needing to remove any great amounts of unconverted starting materials and to recycle them into the process. Moreover, it should be possible to work at minimum pressures. In order to minimize by-product formation, low temperatures should be employed. The workup should be simple and lead to a high product purity.

This object is achieved by a process for preparing unsymmetric secondary tert-butylamines of the formula I by reductively aminating aldehydes of the formula II with tert-butylamine and hydrogen in the liquid phase in the presence of hydrogenation catalysts, comprising the following steps:

(i) providing tert-butylamine and the hydrogenation catalyst in a pressure vessel, (ii) adding hydrogen and continuously adding an aldehyde of the formula II $$R\text{---}CHO \qquad \text{II}$$

where R is selected from the group of hydrogen, linear or branched aliphatic radical having 1 to 15 carbon atoms, cycloaliphatic radical having 5 to 10 carbon atoms, a substituted or unsubstituted phenyl radical and a phenylalkyl radical, and the ratio of hydrogen to aldehyde of the formula II is at least equimolar, (iii) keeping the temperature during the addition of the aldehyde in step (ii) within the range from 50 to 150° C. and keeping the total pressure during the addition of the aldehyde in step (ii) within the range from 2 to 120 bar, (iv) dewatering the hydrogenation output from step (iii) which comprises the secondary tert-butylamine which is formed and is of the formula I

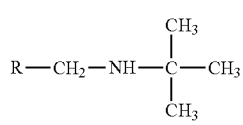

and the water of reaction, and (v) subsequently fractionally distilling the dewatered hydrogenation output from step (iv).

The invention reaction can be described by the following formula equation:

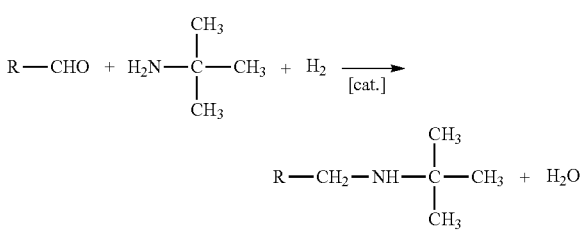

The reductive amination is performed in the liquid phase. This means that tert-butylamine, with a boiling point of 44° C. at a pressure of 1013 mbar, can be supplied to the pressure vessel in liquid form.

It may be advantageous to perform the reductive amination in the presence of a solvent which is inert under the reaction conditions. "Inert" is understood to mean that the solvent does not take part in the reaction as a reagent. Examples of useful solvents for this purpose include N-methylpyrrolidone, or ethers such as tetrahydrofuran, dioxane, ethylene glycol dimethyl ether. The solvent may be initially charged together with the tert-butylamine and the catalyst, supplied with the aldehyde II, or divided between the initially charged reaction mixture and the aldehyde II supplied. However, preference is given to working in the absence of a solvent.

The catalysts used for the aminating hydrogenation may be all hydrogenation catalysts known to those skilled in the art. These are described in Houben-Weyl, Methoden der organischen Chemie, 4th edition, volume 11/1, page 602, and Handbook of Heterogeneous Catalysis, 2nd edition, volume 7, 2008, Wiley VCH, page 3554. Preferred hydrogenation catalysts are the metals and/or metal oxides selected from the group of nickel, cobalt, ruthenium, rhodium, palladium, platinum, copper, especially the metals from the group of palladium, cobalt, nickel and ruthenium, and mixtures of these metals. Cobalt, nickel and copper can also be used as Raney catalysts. Particular preference is given to palladium, cobalt and ruthenium. Very particular preference is given to palladium as a hydrogenation catalyst with which particularly good yields for the inventive reaction can be achieved. The metals can be used as such, or else applied to supports. Preferred supports are selected from the group of aluminum oxide, silicon dioxide, titanium dioxide, zirconium dioxide and activated carbon. Particular preference is given to the supported metals. Preferred supports are activated carbon, aluminum oxide and titanium dioxide. A very particularly preferred support is activated carbon. A very especially preferred hydrogenation catalyst is palladium on activated carbon (Pd/carbon).

The amount of hydrogenating metal (without catalyst support) is 0.001 to 10% by weight, preferably 0.1 to 5% by weight, based on the total mass of tert-butylamine used.

The hydrogenation catalysts are initially charged in the pressure vessel with tert-butylamine and optionally the solvent, and mixed intensively by stirring with the aldehyde II supplied. The aldehyde of the formula II is supplied to the tert-butylamine initially charged in the reaction vessel and the hydrogenation catalyst, and to any solvent present, preferably in such a way that homogeneous mixing of the reactants is possible. Preference is given to adding the aldehyde of the formula II within 30 to 600 minutes, more preferably within 120 to 480 minutes, especially preferably within 300 to 420 minutes. In the case of addition of the aldehyde II, it may be advantageous to reduce the metering rate after addition of ⅔ of the total amount of aldehyde II by 50% (metering ramp). On completion of addition of the aldehyde of the formula II, it is preferred to observe a period of continued stirring in the range from 0.5 to 12 hours, more preferably from 0.5 to 2 hours under the conditions selected.

Suitable pressure vessels are any stirred hydrogenation reactors which are known to those skilled in the art and in which the catalyst can be suspended and/or arranged in fixed bed form. Preference is given to stirred hydrogenation reactors which comprise catalyst baskets.

For the process according to the invention, the aldehydes of the formula II used may be any aldehydes whose R radical is selected from the group of hydrogen, linear or branched aliphatic radical having 1 to 15 carbon atoms, cycloaliphatic radical having 5 to 10 carbon atoms, a substituted or unsubstituted phenyl radical and a phenylalkyl radical. For the process according to the invention, preference is given to using aldehydes of the formula II whose R radical is an aliphatic radical having 1 to 15 carbon atoms, more preferably having 1 to 7 carbon atoms, or a cycloaliphatic radical having 5 to 10 carbon atoms. Formaldehyde can be used as an aqueous solution which comprises 1 to 50% by weight of formaldehyde, or in the form of a paraformaldehyde, dissolved in organic solvents. Preferred aldehydes of the formula II are selected from the group of acetaldehyde, propionaldehyde, n-butyraldehyde, i-butyraldehyde, sec-butyraldehyde, pivalaldehyde, n-pentanal, n-hexanal, 2-ethylhexanal, 2-methylpentanal, 3-methylpentanal, 4-methylpentanal, n-octanal, n-decanal, n-undecanal, n-dodecanal, 11-methyldodecanal, cyclopentylaldehyde, cyclohexylaldehyde, cycloheptylaldehyde, adamantylaldehyde, phenylacetaldehyde and benzaldehyde or mixtures of these aldehydes. Particular preference is given to acetaldehyde, propionaldehyde, n-butyraldehyde, i-butyraldehyde, sec-butyraldehyde, pivalaldehyd, n-pentanal, n-hexanal, 2-methylpentanal, 3-methylpentanal, 4-methylpentanal, cyclohexylaldehyde or mixtures of these compounds. Acetaldehyde, propionaldehyde, butyraldehyde, cyclohexanealdehyde and benzaldehyde are especially preferred. Very particular preference is given to acetaldehyde.

Since side reactions such as the decarbonylation and the aldol condensation of the aldehydes of the formula II used and the formation of tertiary amines of the formula III

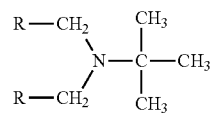

increase with rising temperature, the process according to the invention is performed at as low as possible a temperature. Low temperatures mean temperatures below 150° C. The range employed is preferably from 50 to 150° C., more preferably from 60 to 130° C., most preferably from 70 to 125° C. When the aldehydes of the formula II used are aromatic aldehydes with a substituted or unsubstituted phenyl radical or phenylalkyl radical as the R radical, the reaction is preferably performed at least 110° C. within the inventive temperature range, in order to optimize the yields.

In the aminating hydrogenation, at least equimolar amounts of hydrogen must be present per mole of aldehyde of the formula II.

The total pressure in the reaction vessel at the particular temperature is composed of the partial pressures of the feedstocks and of the reaction products, i.e. hydrogen, tert-butylamine, aldehyde II, amine I, water and any solvent additionally used. Injection of hydrogen increases the pressure to the desired reaction pressure. In order to compensate for the consumption of hydrogen, the total pressure is kept constant during the reaction time by injecting further hydrogen.

The total pressure is 2 to 120 bar, preferably 3 to 50 bar, very preferably 4 to 20 bar, especially preferably 5 to 10 bar.

The molar ratio of tert-butylamine to aldehyde of the formula II should not be greater than 1:1.4. A preferred ratio of tert-butylamine to aldehyde of the formula II is in the region of 1:1.3, more preferably 1:1.2, even more preferably 1:1.1 and very especially preferably 1:1.

The process according to the invention enables the preparation of secondary amine of the formula I in high yield. At the same time, the formation of tertiary amine of the formula III from other possible by-products of the reaction is, however, also substantially avoided. The process according to the invention thus has not only the high yield but also a high selectivity for the preparation of the secondary amine of the formula I.

On completion of hydrogenation according to step (ii) and step (iii) of the process according to the invention, the hydrogenation catalyst, if it was suspended, after cooling and decompression of the hydrogenation output, is removed by filtration, centrifugation or crossflow filtration. If the catalyst was in fixed bed form, the hydrogenation output is removed from the reactor. The catalyst can be recycled into the next semicontinuous hydrogenation. In this case, it may be necessary to compensate for losses of original amount of catalyst by attrition and/or deactivation by adding fresh catalyst.

The hydrogenation output freed of catalyst comprises, as well as the inventive amine of the formula I, as by-products, small amounts of tertiary amines of the formula III.

In addition, small amounts of alcohols R—CH$_2$OH which have been formed by reduction of aldehydes II, of tert-butylamine and of aldehyde II may be present. Small amounts are understood in each case to mean less than 5% by weight, preferably less than 3% by weight and more preferably less than 1% by weight of the compounds mentioned, based on the catalyst-free hydrogenation output.

The reductive amination forms about 5 to 20% by weight of water, based on the catalyst-free hydrogenation output. The secondary unsymmetric tert-butylamines I form azeotropes with water. It is therefore possible to remove by distillation only mixtures consisting of water of reaction and amine I from the hydrogenation output.

EP-B 1312599 and EP-B 1312600 describe the separation of amine-containing mixtures which comprise one or more amines, water, low boilers and high boilers. However, the separation of a secondary tert-butylamine hydrogenation mixture is not described. The separation is effected by
(a) the distillative removal of low boilers from the amine-containing mixture,
(b) optional distillative removal of high boilers from the amine-containing mixture,
(c) extraction of the amine-containing mixture with sodium hydroxide solution to obtain an aqueous first phase comprising sodium hydroxide solution, and an aqueous-organic second phase comprising amine,
(d) distillation of the aqueous-organic second phase from step (c) to obtain amine/water azeotrope and essentially anhydrous amine, and recycling the amine/water azeotrope into the extraction step (c).

The essentially anhydrous amine has to be purified further by distillation. In a working example, the component steps of the workup are demonstrated on a hydrogenation output which has been obtained by reductive amination of 1,5-pentanediol with ammonia to form piperidine.

In the process according to the invention, the catalyst-free hydrogenation output can also be worked up by a distillation and breaking the amine/water azeotropes with sodium hydroxide solution. Distillation and breaking of the amine/water azeotrope can be performed continuously, preferably batchwise.

If the catalyst-free hydrogenation output is to be worked up by distillation and breaking of the azeotropes, in contrast to the prior art, the amine I/water azeotrope is first broken by treating the catalyst-free hydrogenation output with aqueous, for example 50% aqueous, sodium hydroxide solution. The concentration of sodium hydroxide in the aqueous solution may be 1 to 75% by weight, preferably 25 to 50% by weight. Instead of sodium hydroxide, it is also possible to use other alkali metal and alkaline earth metal hydroxides. After extracting the hydrogenation output with the aqueous sodium hydroxide solution, the latter is removed by phase separation. The residual water content of the organic phase can be determined, for example, by Karl Fischer titration. The amount of sodium hydroxide solution required for the removal of water can be determined by a few preliminary tests.

The extraction apparatus used for the extraction with sodium hydroxide solution may have a one-stage or multistage configuration, for example a single mixer-settler extractor. Multistage extractions are, for example, extraction columns or extraction cascades. Suitable extraction columns are, for example, columns with random packing, sieve-tray columns, cascade columns, pulsed columns, rotary columns and centrifugal columns. An extraction cascade is, for example, a plurality of mixer-settler extractors which are connected in series and may also be configured in a space-saving manner as a tower extractor or box extractor. When the extractor has multiple stages, preference is given to a countercurrent extraction column having generally 1 to 25 and preferably 4 to 10 theoretical plates. This is generally operated at a pressure at which all components of the extraction mixture are present below their boiling points, and a viscosity of the two phases at which dispersion of the two phases is possible without any problem is additionally established. The temperature is generally in the range from 5 to 200° C., preferably in the range from 20 to 70° C., more preferably in the range from 40 to 50° C. After phase separation, the aqueous phase comprising sodium hydroxide solution is discharged from the process as a waste stream.

If the aqueous sodium hydroxide solution removed comprises significant amounts of secondary tert-butylamine of the formula I, aldehyde of the formula II and/or tert-butylamine, these compounds can be recovered by extraction with organic solvents. Significant amounts are understood to mean more than 10% by weight, preferably more than 5% by weight, more preferably more than 2% by weight, based on the anhydrous and catalyst-free hydrogenation output.

Useful organic solvents include, for example, aliphatic, cycloaliphatic or aromatic hydrocarbons which have a miscibility gap with aqueous sodium hydroxide solution. Examples of such hydrocarbons are n-hexane, n-octane, cyclohexane, toluene and ethylbenzene, or mixtures of these compounds.

The aqueous sodium hydroxide solution phase is removed from the hydrocarbon phase by phase separation. The hydrocarbon is removed by distillation from the hydrocarbon phase. The secondary tert-butylamine of the formula I recovered, the aldehyde of the formula II and/or tert-butylamine can be combined with the majority of crude secondary tert-butylamine of the formula I and purified by distillation.

It is additionally possible to break the azeotrope composed of secondary tert-butylamine of the formula I and water by adding hydrocarbons to the catalyst-free hydrogenation output, by subsequently distilling hydrocarbon/water heteroazeotropes out of the hydrogenation output, then removing the water phase from the hydrocarbon phase and recycling the hydrocarbon phase into the distillation.

A further option is first to remove the azeotrope composed of secondary tert-butylamine of the formula I and water by distillation and only then to carry out the dewatering by treatment with sodium hydroxide solution or distillation with hydrocarbons.

Finally, the removal of water by treatment with sodium hydroxide solution can be connected to the removal of water by distillation with hydrocarbons. In this case, the majority of water in the hydrogenation output is removed by treatment with sodium hydroxide solution, for example by one-stage extraction with sodium hydroxide solution, the phases are separated, the sodium hydroxide solution phase is extracted with a hydrocarbon, the hydrocarbon phase is removed from the sodium hydroxide solution phase, the hydrocarbon phase removed is combined with the catalyst-free hydrogenation output, and the water still present or a portion thereof is removed by azeotropic distillation.

In a particularly preferred process, the water is not completely removed before the distillative workup of the hydrogenation output. The water content of the hydrogenation output may, for example, be below 5% by weight, preferably below 3% by weight, more preferably below 0.9% by weight. When only a small amount of residual water is present, only a small amount of secondary tert-butylamine of the formula I is discharged as an azeotrope with water in the course of distillation. Small amounts of azeotrope, for example those which comprise less than one mol % of secondary tert-butylamine of the formula I, based on tert-butylamine used, can optionally be discarded. However, it is also possible to recycle the azeotrope into the extraction with sodium hydroxide solution. It is advantageous to need only a one-stage treatment of the hydrogenation output with sodium hydroxide solution. In addition, no fine adjustment of the amount of sodium hydroxide solution is needed in order also to remove the last residues of water.

The hydrogenation output which is anhydrous or comprises only less than 5%, preferably less than 3% and more preferably less than 1% by weight of water can be purified further by fractional distillation. The distillation can be performed continuously, preferably batchwise. In this distillation, if present, unconverted tert-butylamine, unconverted aldehyde of the formula II and alcohols formed from the aldehydes distil overhead in first mixed fractions. These are followed by the inventive secondary tert-butylamine of the formula I, which is likewise distilled off overhead. If present, tertiary amines of the formula III and high boilers remain in the bottoms. Insufficiently pure fractions comprising products of value can be recycled into the distillation.

For the fractional distillation, customary apparatus is useful, as described, for example, in Kirk-Othmer, Encyclopedia of Chemical Technology, 3rd edition, volume 7, John Wiley and Sons, New York, 1979, pages 870 to 881, such as sieve tray columns, bubble-cap tray columns, columns with structured packing or columns with random packing.

Fractional distillation achieves purities of the secondary tert-butylamines of the formula I of more than 98 area %, especially more than 99 area %, more preferably of more than 99.5 area %, especially more than 99.9 area % (GC analysis)

For the continuous workup according to EP-B 1,312,599 and EP-B 1,312,600 (FIGS. 1 and 2), three to four tailored distillation columns and one extraction apparatus are required.

In the preferred inventive batchwise workup, in contrast, only one distillation column and one extraction apparatus are used.

EXAMPLES

General Procedure for the Aminating Hydrogenation of Aldehydes with tert-butylamine The experiments were carried out in a 500 ml Büchi laboratory autoclave which was equipped with a disk stirrer, baffles and a feed pump. The nitrogen-inertized autoclave was initially charged with tert-butylamine and hydrogenation catalyst, and heated to the reaction temperature while stirring. The reaction pressure was established by injecting hydrogen. Within the time specified in each case, the aldehyde of the formula II was pumped in. In the case of acetaldehyde, the reservoir vessel and the feed pump were cooled owing to the relatively high acetaldehyde vapor pressure. The hydrogen pressure was kept constant using a RECO valve. Once the metered addition of aldehyde had concluded, the reaction mixture was stirred under the reaction conditions for a further 0.5 to three hours, then cooled and decompressed.

After removal of the catalyst, the hydrogenation output was analyzed by gas chromatography. For this purpose, an RTX5-amine GC column was used (30 m, 0.32 mm, 1.5 μm, 60-5'-15-280/20, helium). The analysis figures are area percentages.

Comparative Examples 1a and 1b and Examples 1c and 1d

Comparison of the Reaction of tert-butylamine, i-propylamine and Ethylamine with Acetaldehyde and Hydrogen Examples 1a, 1b and 1c were carried out with in each case 1.93 mol of amine (ethylamine, i-propylamine or tert-butylamine) at 85° C. and 6 bar, or, in the case of ethylamine, 8 bar, in the presence of a palladium catalyst (H0-50, 5% Pd on carbon). The molar ratio of aldehyde to amine was 1.05; the amount of hydrogenation catalyst was 2.0% by weight, based on the total amount of amine. The acetaldehyde was supplied to the reactor within 6 hours. The continued stirring time was 1 hour or 2 hours (i-propylamine).

In example 1d, tert-butylamine was reacted with acetaldehyde in an analogous manner to that in example 1c, but at a pressure of 10 bar.

Table 2a compiles the reaction conditions and yields, and table 2b the results of the gas chromatography analysis.

Inventive example 1c shows that the hydrogenation output, calculated without water, consists to an extent of >94 area % of ethyl-tert-butylamine target product. The tert-butylamine and acetaldehyde feedstocks were converted apart from 2.1 and 0.2 area % respectively, and the amount of the tertiary diethyl-tert-butylamine was only 3 area %.

When, in contrast, according to noninventive examples 1b and 1a, isopropylamine or ethylamine are used instead of tert-butylamine, the amounts of secondary isopropyl- and ethylamine surprisingly fall to only 70 area % and only 53 area % respectively. In parallel, the amount of unconverted starting amine rises significantly and the amount of undesired tertiary amine rises substantially (table 2b).

It is surprising that, in accordance with the invention, compared to the prior art, higher yields are achieved at 94 area % without a significant excess of starting amine (table 1), without solvents and at low pressure (table 1). It is additionally surprising that similarly high yields are possible at low pressure without the use of aqueous sodium hydroxide solution (table 1).

The process according to the invention leads, by virtue of substantial conversion of the starting components and low formation of tertiary amines of the formula III, to a simplified workup with reduced energy requirement at high purity of the secondary tert-butylamine of the formula I.

It was also unforeseeable that significantly higher yields of secondary tert-butylamines of the formula I are achievable in accordance with the invention with tert-butylamine than with i-propylamine and ethylamine.

Examples 2a and 2b

In an analogous manner to that in example 1c, 1.5 mol of tert-butylamine were reacted with n-propionaldehyde (example 2a) or n-butyraldehyde (example 2b) to give the corresponding secondary amines (tert-butylpropylamine and n-butyl-tert-butylamine respectively), and they were then analyzed by gas chromatography. For these reactions too, yields of 93.6 area % (example 2a) and 95.7 area % (example 2b) of the corresponding secondary amines were achieved.

For example 2a, the following proportions of by-products were found in the reaction mixture by gas chromatography: propionaldehyde (0.5 area %), propanol (0.6 area %), tert-butylamine (0.7 area %) and tertiary amine (1.3 area %).

And, for example 2b, the following proportions of by-products were found in the reaction mixture by gas chromatography: n-butyraldehyde (0.4 area %), n-butanol (0.3 area %), tert-butylamine (0.3 area %) and tertiary amine (0.9 area %).

Examples 3a and 3b

In an analogous manner to that in example 1c, except using 4.0% by weight of hydrogenation catalyst, based on the total amount of amine, 1 mol of tert-butylamine was reacted with cyclohexanal (example 3a) or benzaldehyde (example 3b) to give the corresponding secondary amines (tert-butylcyclohexylmethylamine and benzyl-tert-butylamine respectively) which were then analyzed by gas chromatography. For these reactions, yields of 87.3 area % (example 3a) and 14.2 area % (example 3b) of the corresponding secondary amines were achieved.

In the gas chromatography analysis for example 3a, tert-butyl cyclohexylmethyl imine (5.7 area %) was identified as the principle by-product. No detectable amounts of the corresponding tertiary amine were found. The amount of the tert-butyl cyclohexylmethyl imine by-product was reduced to a proportion of 2.3 area % by extending the continued stirring time by a further 6 h, in favor of the yield of tert-butylcyclohexylmethylamine, which rose to 90.6 area %.

In example 3b, the gas chromatography analysis found, as by-products, principally unconverted tert-butylamine (26.1 area %), benzyl alcohol (54 area %) and toluene (5.4 area %). No detectable amounts of the corresponding tertiary amine were formed. Increasing the reaction temperature to 100° C. enhanced the yield of benzyl-tert-butylamine to 19.6 area % while simultaneously reducing the formation of benzyl alcohol. Further increasing the reaction temperature to 120° C. enhanced the yield further to 83.0 area %. The by-products found at this temperature were principally unconverted tert-butylamine (3.4 area %), benzyl alcohol (8.1 area %) and toluene (5.5 area %).

(iii) keeping the temperature during the addition of the aldehyde in (ii) within the range from 50 to 150° C. and keeping the total pressure during the addition of the aldehyde in (ii) within the range from 2 to 120 bar, (iv) dewatering the hydrogenation output from (iii) which comprises the secondary tert-butylamine which is formed and is of the formula I

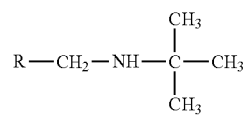

where R is defined above and the water of reaction, and (v) subsequently fractionally distilling the dewatered hydrogenation output from (iv).

2. The process according to claim 1, wherein (ii) involves, after addition of the aldehyde, further stirring for a period of 0.5 to 12 hours while maintaining the pressure and temperature conditions selected for the addition of the aldehyde.

3. The process according to either of claims 1 and 2, wherein the total pressure is kept at 4 to 20 bar during (ii).

TABLE 2a

| Example No. | Prim. amine | Aldehyde | Molar ratio of aldehyde/amine | Catalyst | Addition | Addition and continued stirring time [h] | Pressure [bar] | Solvent or addition | Yield |
|---|---|---|---|---|---|---|---|---|---|
| 1 a | Ethylamine | Acetaldehyde | 1:1.05 | H 0-50 (5% by weight) | Amine initially charged | 7 (6 + 1) | 8 | — | 53 |
| 1 b | i-Propylamine | | | | | 8 (6 + 2) | 6 | — | 70 |
| 1 c | tert-Butylamine | | | | | 7 (6 + 1) | 6 | — | 94 |
| 1 d | | | | | | 7 (6 + 1) | 10 | — | 94 |

TABLE 2b

| | | | Hydrogenation output (GC area percent) | | | | | |
|---|---|---|---|---|---|---|---|---|
| Example No. | Prim. amine | Aldehyde | Acetaldehyde | Ethanol | Amine | Sec. amine I | Tert. amine III | Total GC area % |
| 1 a | Ethylamine | Acetaldehyde | — | 0.01 | 7.9 | 52.9 | 28.3 | 89.1 |
| 1 b | Isopropylamine | | 0.03 | — | 6.3 | 70.2 | 19.2 | 95.7 |
| 1 c | tert-Butylamine | | 0.2 | 0.2 | 2.1 | 94.0 | 3.0 | 99.5 |
| 1 d | | | 0.4 | 0.6 | 0.4 | 94.3 | 3.4 | 99.1 |

The invention claimed is:

1. A process for preparing an unsymmetric secondary tert-butylamine of the formula I by reductively aminating an aldehyde of the formula II with tert-butylamine and hydrogen in the liquid phase in the presence of a hydrogenation catalyst, comprising:

(i) providing tert-butylamine and the hydrogenation catalyst in a pressure vessel, (ii) adding hydrogen and continuously adding an aldehyde of the formula II

R—CHO   II where R is selected from the group of hydrogen, a linear or branched aliphatic radical having 1 to 15 carbon atoms, a cycloaliphatic radical having 5 to 10 carbon atoms, a substituted or unsubstituted phenyl radical, and a phenylalkyl radical, and the ratio of hydrogen to aldehyde of the formula II is at least equimolar, 4. The process according to claim 1, wherein the temperature is kept at 70 to 125° C. during (ii).

5. The process according to claim 1, wherein the molar ratio of tert-butylamine used in (i) to aldehyde of the formula II supplied in (ii) is in the range from 1:1 to 1:1.4.

6. The process according to claim 1, wherein the aldehyde of the formula (II) is supplied in (ii) within 30 to 600 minutes.

7. The process according to claim 1, wherein (i) to (iii) are performed in the presence of a solvent which is inert under the reaction conditions.

8. The process according to claim 1, wherein the hydrogenation catalyst comprises a catalytically active material that comprises a metal and/or metal oxide selected from the group of nickel, cobalt, ruthenium, rhodium, palladium, platinum, copper and mixtures of these metals and/or metal oxides.

9. The process according to claim 8, wherein the catalytically active material of the hydrogenation catalyst comprises the metal palladium.

10. The process according to claim 1, wherein the hydrogenation catalyst comprises a catalytically active material that has been applied to an activated carbon support.

11. The process according to claim 1, wherein the hydrogenation is a suspension hydrogenation, and the hudrogenation catalyst is removed from the hydrogenation output before the dewatering in (iv) and recycled into the hydrogenation stage in (i).

12. The process according to claim 11, wherein the catalyst-free hydrogenation output is dewatered with the aid of aqueous sodium hydroxide solution.

13. The process according to claim 11, wherein the catalyst-free hydrogenation output is dewatered by azeotropic distillation with hydrocarbons.

14. The process according to claim 1, which is operated semicontinuously.

15. The process according to claim 1, wherein the hydrogenation catalyst is palladium on activated carbon.

16. The process according to claim 1, wherein the aldehyde of the formula II is selected from the group consisting of acetaldehyde, propionaldehyde, n-butyraldehyde, i-butyraldehyde, sec-butyraldehyde, pivalaldehyde, n-pentanal, n-hexanal, 2-ethylhexanal, 2-methylpentanal, 3-methylpentanal, 4-methylpentanal, n-octanal, n-decanal, n-undecanal, n-dodecanal, 11-methyldodecanal, cyclopentylaldehyde, cyclohexylaldehyde, cycloheptylaldehyde, adamantylaldehyde, phenylacetaldehyde, benzaldehyde and mixtures of these aldehydes.

17. The process according to claim 1, wherein the aldehyde of the formula II is selected from the group consisting of acetaldehyde, propionaldehyde, n-butyraldehyde, i-butyraldehyde, sec-butyraldehyde, pivalaldehyd, n-pentanal, n-hexanal, 2-methylpentanal, 3-methylpentanal, 4-methylpentanal, cyclohexylaldehyde and mixtures of these compounds.

18. The process according to claim 1, wherein the aldehyde of the formula II is acetaldehyde.

19. The process according to claim 15, wherein the aldehyde of the formula II is acetaldehyde.

20. The process according to claim 1, wherein the molar ratio of tert-butylamine used in (i) to aldehyde of the formula II supplied in (ii) is in the range from 1:1 to 1:1.1.

* * * * *